United States Patent
Becker

(10) Patent No.: US 11,491,316 B2
(45) Date of Patent: Nov. 8, 2022

(54) LUER TO LUER TISSUE MORSELIZER

(71) Applicant: Hilton Becker, Boca Raton, FL (US)

(72) Inventor: Hilton Becker, Boca Raton, FL (US)

(*) Notice: Subject to any disclaimer, the term of this patent is extended or adjusted under 35 U.S.C. 154(b) by 359 days.

(21) Appl. No.: 16/192,459

(22) Filed: Nov. 15, 2018

(65) Prior Publication Data
US 2019/0151642 A1 May 23, 2019

Related U.S. Application Data

(60) Provisional application No. 62/589,782, filed on Nov. 22, 2017.

(51) Int. Cl.
*A61M 39/10* (2006.01)
*A61B 17/3207* (2006.01)

(52) U.S. Cl.
CPC . *A61M 39/10* (2013.01); *A61B 2017/320775* (2013.01); *A61M 2039/1033* (2013.01); *A61M 2039/1061* (2013.01); *A61M 2039/1077* (2013.01); *A61M 2039/1083* (2013.01); *A61M 2202/08* (2013.01)

(58) Field of Classification Search
CPC .......... A61M 39/10; A61M 2039/1033; A61M 2039/1061; A61M 2039/1072; A61M 2039/1077; A61M 2039/1083; A61M 2039/1088; A61M 5/16813; A61M 5/3007; A61M 5/2053; A61M 1/0094; A61B 2017/320775; F16K 3/0281
See application file for complete search history.

(56) References Cited

U.S. PATENT DOCUMENTS

| 4,629,455 | A | * | 12/1986 | Kanno | A61M 5/344 285/332 |
| 2007/0129705 | A1 | * | 6/2007 | Trombley, III | A61M 39/12 604/523 |
| 2008/0103482 | A1 | * | 5/2008 | Fangrow | A61M 39/10 604/523 |
| 2008/0284167 | A1 | * | 11/2008 | Lim | A61M 39/10 285/382 |
| 2013/0123747 | A1 | * | 5/2013 | Tremolada | A61M 19/00 604/506 |

* cited by examiner

*Primary Examiner* — William R Carpenter
*Assistant Examiner* — Justin L Zamory
(74) *Attorney, Agent, or Firm* — Ken Motolenich-Salas; Jeffrey D. Moy; Weiss & Moy, P.C.

(57) ABSTRACT

A morselizer comprising (a) a hollow cylindrical structure with an inner wall and an outer wall and comprising a first end section, a second end section, and a center section extending axially between the first end section and the second end section providing a substantially axial liquid pathway therein; (b) wherein each end section comprises a axially and radially hollow luer fitting that is attachable to a structure with a complementarily sized luer fitting; and (c) one or more blades extending transversally across the inner diameter of the center section wherein (i) each blade is comprised of a plurality of ends, including a posterior end secured to at least the center wall section inner wall at a center section inner wall first position and an anterior end proximal a center section inner wall second position opposite the center section inner wall first position, with a gap positioned between the blade anterior end and the center section inner wall second position, and (ii) at least two ends comprise cutting ends.

5 Claims, 5 Drawing Sheets

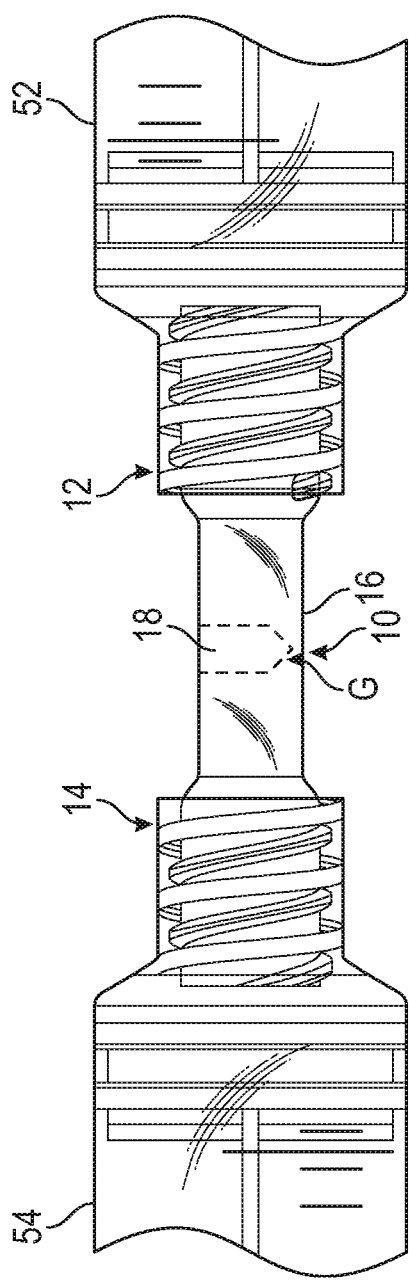
FIG. 7
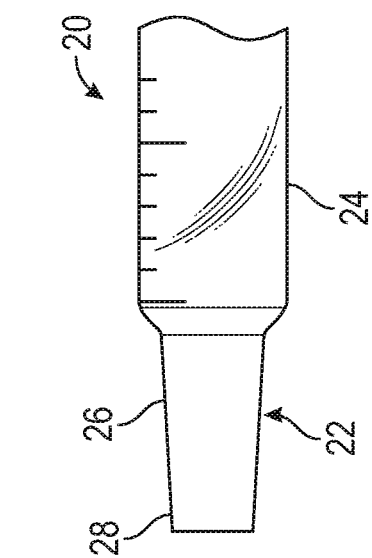
FIG. 8
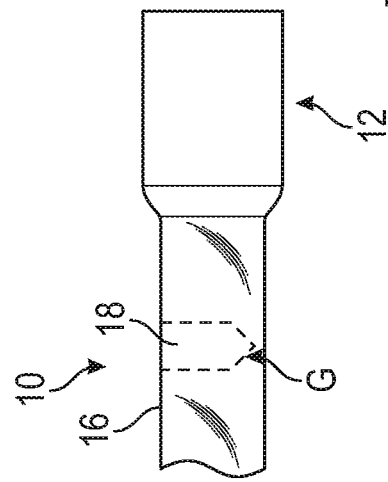

LUER TO LUER TISSUE MORSELIZER

CLAIM OF PRIORITY

This application claims the benefit of U.S. Provisional Application 62/589,782 filed Nov. 22, 2017.

FIELD OF THE INVENTION

The present invention relates to an apparatus with luer or similar fitting for use in atraumatically resizing biologic material.

BACKGROUND OF THE INVENTION

The attachment of a first structure with a male tapered fitting to a second structure with a conforming taper providing a female tapered fitting that is mateable to the first structure male tapered fitting, with a portion of the male tapered fitting of the first structure accommodated within a portion of the female tapered fitting of the second structure, such as the one described in U.S. Pat. No. 5,312,377 to Dalton, is widely used in the medical field to connect two liquid conduits end to end. These so-called luer fittings provide an ISO-standardized system (ISO 80369, "Small-Bore Morselizer Standards", referencing ISO 594-1 and ISO 594-2 therein) across small-scale liquid fittings in order to make leak-free connections between two structures, such as a male luer fitting of a structure mateably attachable to a female luer fitting of another structure. These luer fittings are (i) common across medical and laboratory instruments to make leak-free/leakproof, mechanically secure connections between two parts, such as to join hypodermic needles to syringes or one catheter to another catheter; and (ii) described as having a male luer fitting and its mating female luer fitting, with the male luer fitting inserted into the female luer fitting and accommodated therein.

Often, such luer fittings are threaded to allow for a threaded attachment between structures with mateable luer fittings, which is commonly referred to as a "luer lock." Such luer lock fittings are divided into two types called one piece luer lock and two piece luer lock or rotating collar luer lock. The one piece luer lock fitting comes as a single mold, with attachment of a structure with such a fitting to another structure with a conforming luer fitting achieved by rotating the entire fitting. In two piece or rotating collar luer lock, a free rotating threaded collar is assembled to the luer fitting and the attachment of a structure with such a fitting to another structure with a conforming luer fitting is achieved by rotating the collar. Alternatively, a structure with a luer fitting that is non-threaded can attach to another structure with a conforming luer taper dimension as that of the first structure, with the luer fittings of the conforming structures pressed together, with frictional forces holding the structures together. This is commonly referred to as luer slip or slip tip. The locking luer lock style luer fittings are generally more secure as one structure with an insertive luer (male) fitting is (i) inserted into another structure with a receptive luer (female) fitting and (ii) twisted to form a luer lock attachment, thus preventing accidental separation of the structures in addition to ensuring no liquids can leak through the attachment. Although not having a threaded attachment augmenting the frictional forces between the two attached structures, the luer slip style fitting allows for quicker attachment between two structures with complementarily sized luer fittings as the attachment simply requires a push of the structures together to form the attachment through the frictional forces between the structures.

In the cosmetic and plastic surgery field, fat injections, also known as fat grafting, are performed. Such procedures can be an effective way to reduce wrinkles, diminish acne scarring, and regain a more youthful appearance. By injecting harvested human fat, cosmetic and plastic surgeons can enhance facial fullness, fill deep creases, soften facial creases and wrinkles, plump up lips, and build up shallow contours. In order to be effective, fat particles injected into the face should be no larger than 1 mm in diameter.

The harvesting of fat with a cannula (a thin tube inserted into the fat tissue) is performed as a means of providing fat particles for injection. A common procedure for harvesting fat, also referred to as "lipoharvest," is called the "Coleman technique" and involves a 2 to 3 mm diameter blunt cannula with a luer fitting attached to a 10-mL syringe with a luer fitting.

When injecting fat into a desired area, the diameter of the injection needle should be similar or slightly larger than the cannula opening(s) in order to avoid damage to the fat particles. In addition, to avoid any unnecessary skin damage when performing fat injection, it is desirable to be able to inject the harvested fat with very narrow-diameter needles, viz., 0.5 to 2.5 mm, to make only small diameter wounds in the skin. However, in order to harvest smaller particles that can pass through such needles, cannulas have been manufactured with smaller holes than traditional cannulas. Although smaller fat particles are obtained, the beneficial fraction comprised of the desirable stromal vascular fraction (SVF) containing a large population of regenerative cells called adipose derived regenerative cells (ADRCs) comprised in part of fibroblasts and stem cells.

As such, it is desirable to harvest larger particles containing the SVF and have a device that allows for atraumatic resizing of the relatively large harvested fat particles without loss of the beneficial SV fraction, while not losing sight of the need for smaller particles to ensure survival until the new blood supply is established to allow for the injection of effectively-sized fat particles (viz., no larger than 1 mm).

SUMMARY OF THE INVENTION

A first aspect of the invention comprises a morselizer comprising (a) a hollow cylindrical structure with an inner wall and an outer wall and comprising a first end section, a second end section, and a center section extending axially between the first end section and the second end section providing an axial liquid pathway therein; (b) wherein each end section comprises an axially and radially hollow luer fitting that is attachable to a structure with a complementarily sized luer fitting; and (c) one or more blades extending transversally across the inner diameter of the center section wherein (i) each blade is comprised of a plurality of ends, including a posterior end secured to at least the center wall section inner wall at a center section inner wall first position and an anterior end proximal a center section inner wall second position opposite the center section inner wall first position, with a gap positioned between the blade anterior end and the center section inner wall second position, and (ii) at least two ends comprise cutting ends.

A second aspect of the invention comprises a morselizer comprising (a) a hollow cylindrical stricture with an inner wall and an outer wall and comprising a first end section, a second end section, and a center section extending axially between the first end section and the second end section providing an axial liquid pathway therein; (b) wherein each end section comprises an axially and radially hollow luer fitting that is attachable to a structure with a complementarily sized luer fitting; (c) wherein the first end section comprises a threaded male luer fitting with a plurality of threads formed on the first end section outer wall; and (d) one or more blades extending transversally across the inner diameter of the center section wherein (i) each blade is comprised of a plurality of ends, including a posterior end secured to at least the center wall section inner wall at a center section inner wall first position and an anterior end proximal a center section inner wall second position opposite the center section inner wall first position, with a gap positioned between the blade anterior end and the center section inner wall second position, and (ii) at least two ends comprise cutting ends.

A third aspect of the invention comprises a morselizer comprising (a) a hollow cylindrical structure with an inner wall and an outer wall and comprising a first end section, a second end section, and a center section extending axially between the first end section and the second end section providing an axial liquid pathway therein; (b) wherein each end section comprises an axially and radially hollow luer fitting that is attachable to a structure with a complementarily sized luer fitting; (c) wherein the first end section comprises a threaded female luer fitting with a plurality of threads formed on the first end section inner wall; and (d) one or more blades extending transversally across the inner diameter of the center section wherein (i) each blade is comprised of a plurality of ends, including a posterior end secured to at least the center wall section inner wall at a center section inner wall first position and an anterior end proximal a center section inner wall second position opposite the center section inner wall first position, with a gap positioned between the blade anterior end and the center section inner wall second position, and (ii) at least two end comprise cutting ends.

A fourth aspect of the invention comprises a morselizer comprising (a) a hollow cylindrical stricture with an inner wall and an outer wall and comprising a first end section, a second end section, and a center section extending axially between the first end section and the second end section providing an axial liquid pathway therein; (b) wherein each end section comprises an axially and radially hollow luer fitting that is attachable to a structure with a complementarily sized luer fitting; (c) wherein the first end section comprises a threaded female-male luer fitting with a plurality of threads formed on the first end section inner wall and the first end section outer wall; and (d) one or more blades extending transversally across the inner diameter of the center section wherein (i) each blade is comprised of a plurality of ends, including a posterior end secured to at least the center wall section inner wall at a center section inner wall first position and an anterior end proximal a center section inner wall second position opposite the center section inner wall first position, with a gap positioned between the blade anterior end and the center section inner wall second position, and (ii) at least two ends comprise cutting ends.

The morselizer allows for atraumatic resizing of material through the morselizer by (I) attaching a first structure with a luer fitting containing fat tissue with its collagen supporting structure (SVF) in a substantially liquid solution to the morselizer by attaching the first structure luer fitting to the luer fitting at the first end section of the morselizer and attaching a second structure with a luer fitting to the luer fitting at the second end of the morselizer; and (II) transferring the solution from the first structure to the morselizer through the first structure-morselizer luer fitting attachment, thence through the morselizer center section where material is resized by the one or more blades positioned in the morselizer center section and through the second end section of the morselizer to the second structure through the second structure-morselizer luer fitting attachment; and, as needed or desired by the user, (III) successively transferring solution from the second structure through the morselizer to the first structure and thence back to the second structure through the morselizer as discussed above at (II).

Although the invention described herein is done so in the context of fat harvesting for injection into the body, the invention is useable in any medical or other scientific procedure wherein substantially solid material, such as particles of a larger size, are atraumatically resized to a smaller desired size.

Further additional, advantageous aspects of the invention, such as variants of the aspects of the invention disclosed above, will become apparent to one of ordinary skill in the art upon review of the following description of the embodiments of the invention and the claims and with reference to the accompanying drawings.

By way of example only, specific embodiments of the invention will now be described, with reference to the accompanying drawings, in which:

DESCRIPTION OF THE DRAWINGS

FIG. 7 is side elevation view of an embodiment of the present invention attached to a plurality of structures, each with a luer fitting;

FIG. 8 is a partial side elevation view of an embodiment of the present invention spaced apart from a structure with a leer fitting.

DETAILED DESCRIPTION OF THE INVENTION

Figure 1:
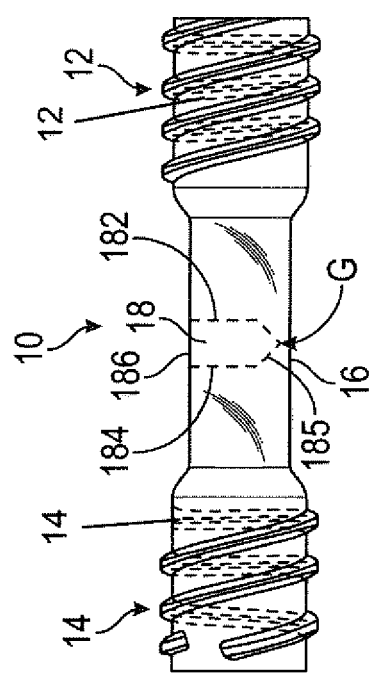
FIG. 1 is a side elevation view of an embodiment of the present invention.

Referring to FIGS. 1-9, morselizer 10 comprises a hollow structure, preferably a thin-walled cylinder, with an inner wall I and an outer wall O and extending axially from a first end and a second end (i.e., the cylinder flat surfaces or bases), wherein both ends are open. Morselizer 10 can be made of any one or more materials known in the art, such as glass, preferably laboratory-grade glass; metal; or plastic, preferably a plastic impervious to and non-degraded by aqueous and organic solutions.

With reference to FIGS. 1-7, morselizer 10 is comprised of first end section 12, second end section 14, and center section 16 extending axially between first end section 12 and second end section 14. The axis of morselizer 10 provides an axial liquid pathway along the hollow structure thereof, extending from first end section 12 to center section 16 and then to second end section 14. Preferably, the inner diameter of morselizer 10 is axially continuous, with the inner diameters of each of first end section 12, second end section 14, and center section 16 the same. Morselizer 10 can have an inner diameter of any size capable of being complementarily sized to structures with small-scale liquid fittings, preferably in the range of 0.1 mm to 10 mm, more preferably in the range of 2 to 5 mm, most preferably in the range of 3 to 4 mm, with an outward bevel extending from center section 16 to first end section 12 and second end section 14.

With reference to FIGS. 1-7, each end section 12/14 of morselizer 10 comprises an axially and radially hollow luer fitting that is attachable to a structure with a complementarily sized luer fitting. The attachment of the morselizer 10 at the each of the end sections 12 and 14 comprising a luer fitting to a structure containing a substantially liquid solution with substantially solid materials suspended therein and having a complementarily sized luer fitting prevents any solution leakage out of the structure during material flow from the structure to morselizer 10. The structure with a complementarily sized luer fitting and attachable to the morselizer 10 at each of the end sections 12/14 can comprise any structure with a luer fitting or luer-compatible fitting (such as a non-luer fitting to luer fitting adapter or other luer to non-luer adaptive structure), such as laboratory glassware, plasticware, or metalware, including, by way of example only and not of limitation, vials, tubes (boiling, test, Thiele), luer lock tip or luer slip tip syringes, burettes, pipettes, cylinders, flasks, beakers, funnels, distilling columns, chromatography columns or other columns used in analytical techniques, or condensers.

The luer fittings comprising end sections 12/14 can be characterized as either (i) "male", with the luer fitting on end section 12/14 of morselizer 10 accommodated within another structure with a luer fitting when the structure is attached to the morselizer 10; or (ii) "female", with the luer fitting on end section 12/14 of morselizer 10 accommodating therein another structure with a luer fitting when the structure is attached to the morselizer 10. Moreover, morselizer end section 12/14 comprising a luer fitting can be threaded or unthreaded, with such threaded or unthreaded morselizer end section 12/14 attachable to a complementarily sized unthreaded or threaded luer fitting on a structure, with (i) the threaded mating and frictional forces generated between the structure and morselizer 10 maintaining the attachment of a threaded morselizer end section 12/14 to a threaded structure and (ii) frictional forces alone maintaining the morselizer-structure attachment in the absence of a mating of threads between the morselizer end section 12/14 and the structure fitting.

With reference to FIGS. 1-7, in an embodiment of the invention, formed on an inner wall (female) (FIGS. 2-3), outer wall (male) (FIGS. 1, 4-7), or both outer and inner walls (male-female, not depicted) of morselizer end section 12/14 comprising a luer fitting are a plurality of threads to allow for a threaded attachment of the end section 12/14 of morselizer 10 to a structure with a complementarily sized threaded or unthreaded luer fitting. In an embodiment of the invention, a threaded luer fitting of end section 12/14 of morselizer 10 is attachable to a structure with a complementarily sized unthreaded luer fitting such as the fitting. In another embodiment of the invention and with reference to FIG. 8, one or more of end sections 12/14 (shown as end section 12 in FIG. 8) comprises an threaded luer fitting that is attachable to a structure 20 with a complementarily sized unthreaded luer fitting 28 by pressing the morselizer 1 and structure 20 together so as to form a luer slip attachment between the morselizer end section and the structure luer fitting, with the attachment of a morselizer end section 12/14 comprising a threaded luer fitting to a complementarily sized unthreaded luer fitting on a structure effectuated from frictional forces generated between the structure and morselizer 10.

Figure 2:
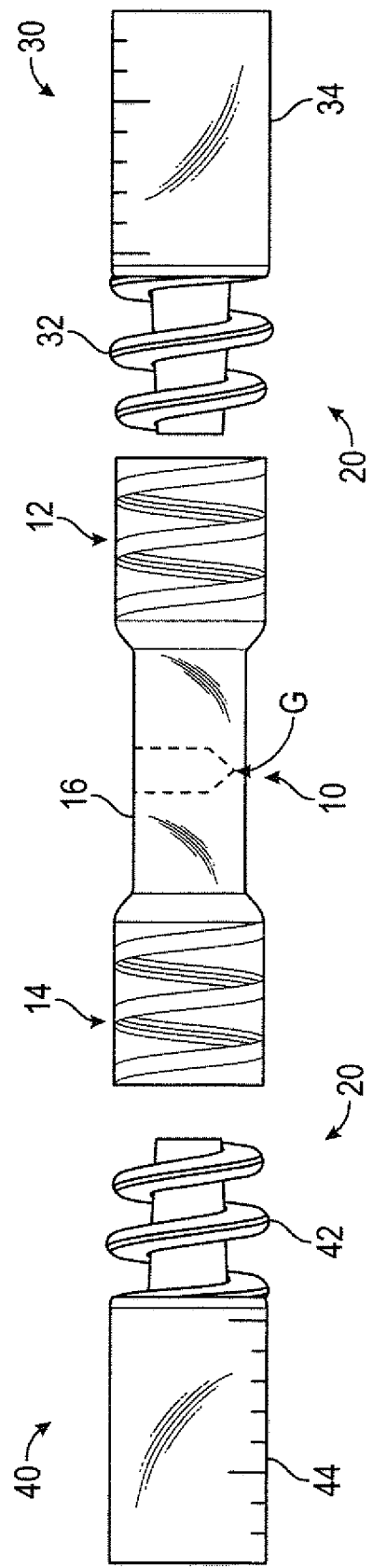
FIG. 2 is a side elevation view of an embodiment of the present invention spaced apart from a plurality of structures, each with a luer fitting.
Figure 3:
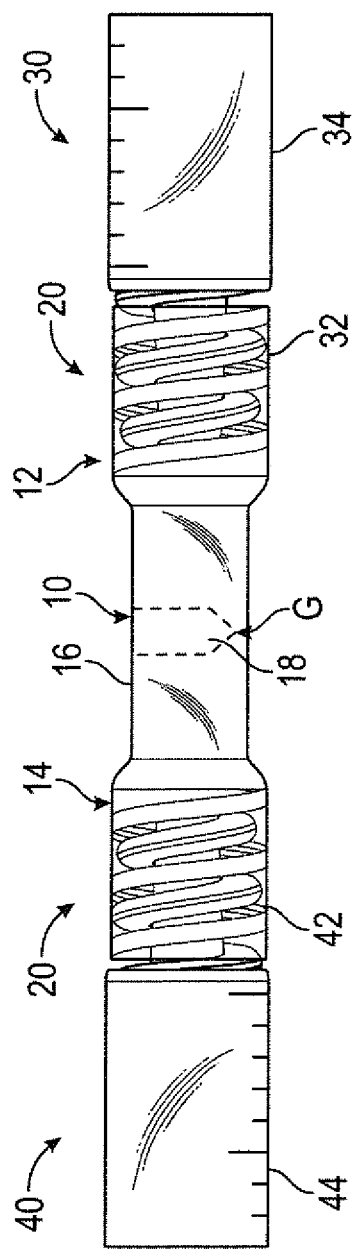
FIG. 3 is a side elevation view of an embodiment of the present invention attached to a plurality of structures, each with a luer fitting.

In an embodiment of the invention and with reference to FIGS. 1-3, one or more of end sections 12 and 14 of morselizer 10 comprises a female luer fitting wherein the inner wall of such end sections 12/14 has disposed thereon a plurality of threads so as to threadedly attach such morselizer end section 12/14 to a structure (30 or 40 as shown in FIGS. 2-3) with a complementarily sized male luer fitting with a plurality of threads formed on the outer wall of such structure (32 or 42, as shown in FIGS. 2-3), such plurality of threads mateable to the plurality of threads of morselizer end section 12/14, with the female luer fitting end section 12/14 securely accommodating therein the male luer fitting (32 or 42 as shown in FIGS. 2-3) of the mateable structure (30 or 40 as shown in FIGS. 2-3).

In an embodiment of the invention, each end section 12 and 14 of morselizer 1 comprises a threaded female luer fitting and can be attached to a structure with a complementarily sized threaded male luer fitting. With reference to FIGS. 2-3, each of first end section 12 and second end section 14 of morselizer 10 comprises an axially and radially hollow female luer fitting with an inner wall having a plurality of threads disposed thereon so as to allow for a threaded attachment of (i) morselizer 10 at first end section 12 to a first structure 30 at the first structure threaded luer fitting 32, with the first structure threaded luer fitting 32 accommodated within the morselizer first end section 12, and (ii) morselizer 10 at second end section 14 to a second structure 40 at the second structure threaded luer fitting 42, with the second structure threaded luer fitting 42 accommodated within the morselizer second end section 14.

In another embodiment of the invention, a female threaded luer fitting end section 12/14 as that described above is attachable to a structure with an unthreaded complementarily sized male luer fitting (such as Luer fitting 28 on structure 20 in FIG. 8) by pressing the morselizer 1 and the attachable structure together (not depicted) forming a Luer slip attachment between the morselizer and the structure.

In another embodiment of the invention, formed on the outer wall of a female threaded luer fitting end section 12/14 is a plurality of threads so as to render end section 12/14 a male-female luer fitting which could alternatively threadedly accommodate in the interior of end section 12/14 a male threaded luer fitting of a structure or be threadedly accommodated within a female threaded luer fitting of a stricture (not depicted).

In an embodiment of the invention and with reference to FIGS. 4-7, one or more of end sections 12 and 14 of morselizer 10 comprises a male luer fitting wherein the outer wall of such end sections 12/14 has disposed thereon a plurality of threads so as to threadedly attach such morselizer end section 12/14 to a structure, such as structure 52/54 as shown in FIGS. 4-7, with a complementarily sized female luer fitting with a plurality of threads formed on the inner wall of such structure 52/54 as shown in FIGS. 4-7, such plurality of threads mateable to the plurality of threads of morselizer end section 12/14, with the female luer fitting of the structure 52/54 securely accommodating therein the male luer fitting of morselizer end section 12/14 as shown in FIGS. 4-7.

In an embodiment of the invention, each end section 12 and 14 of morselizer 1 comprises a threaded male luer fitting and can be attached to a structure with a complementarily sized threaded female luer fitting. With reference to FIGS. 4-7, each of first end section 12 and second end section 14 of morselizer 10 comprises an axially and radially hollow male luer fitting with an outer wall having a plurality of threads disposed thereon so as to allow for a threaded attachment of (i) morselizer 10 at first end section 12 to a first structure at the first structure threaded female Luer fitting 52, with the male fitting of first end section 12 accommodated within the first structure female luer fitting 52 and (ii) morselizer 10 at second end section 14 to a second structure 40 at the second structure threaded female luer fitting 42, with the male fitting of second end section 14 accommodated within the second structure female luer fitting 42.

In another embodiment of the invention, a male threaded luer fitting end section 12/14 as that described above is attachable to a structure with an unthreaded complementarily sized female luer fitting by pressing the morselizer 1 and the attachable structure together (not depicted).

In another embodiment of the invention, formed on the inner wall of a male threaded luer fitting end section 12/14 is a plurality of threads so as to render end section 12/14 a male-female luer fitting which could alternatively threadedly accommodate a male threaded luer fitting of a structure in the interior of end section 12 or be threadedly accommodated within a female threaded luer fitting of a structure (not depicted).

Figure 9:
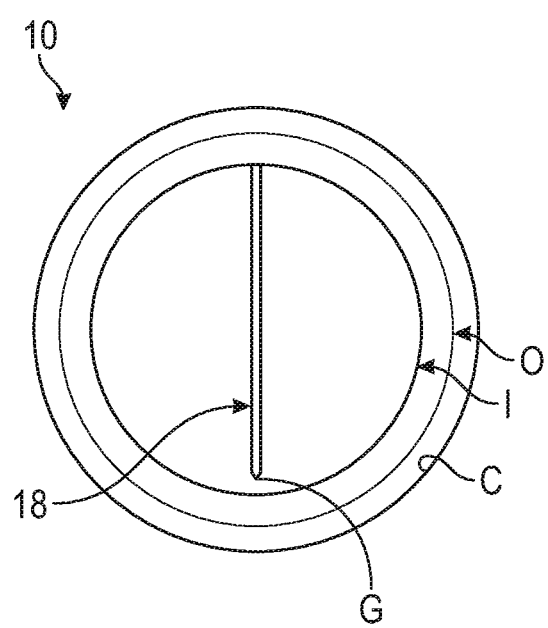
FIG. 9 is a cross-sectional end view of an embodiment of the present invention.

In some embodiments of the invention and with reference to FIG. 9, one or more end sections 12/14 of morselizer 10 has attached to and overlaying the outer wall O of such one or more end sections 12/14 a collar C, with the collar C having an inner wall proximal the outer wall O of morselizer end section 12/14 and having formed thereon a plurality of threads, wherein the collar C is freely rotatable and, when rotated, partially axially displaceable from morselizer outer wall O of morselizer end section 12/14 to allow for a threaded attachment of the collar C to a structure with a complementarily sized threaded luer fitting to form a two piece rotating collar luer lock attachment between morselizer 10 and the structure, with the structure luer fitting accommodated within the inner wall of the collar C.

Figure 4:
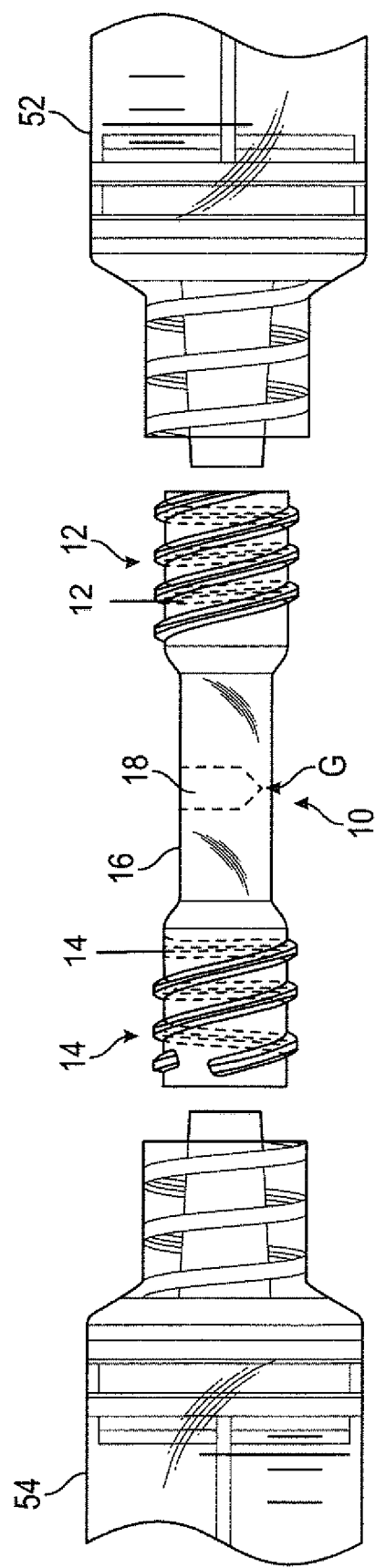
FIG. 4 is a side elevation view of an embodiment of the present invention spaced apart from a plurality of structures, each with a luer fitting.
Figure 5:
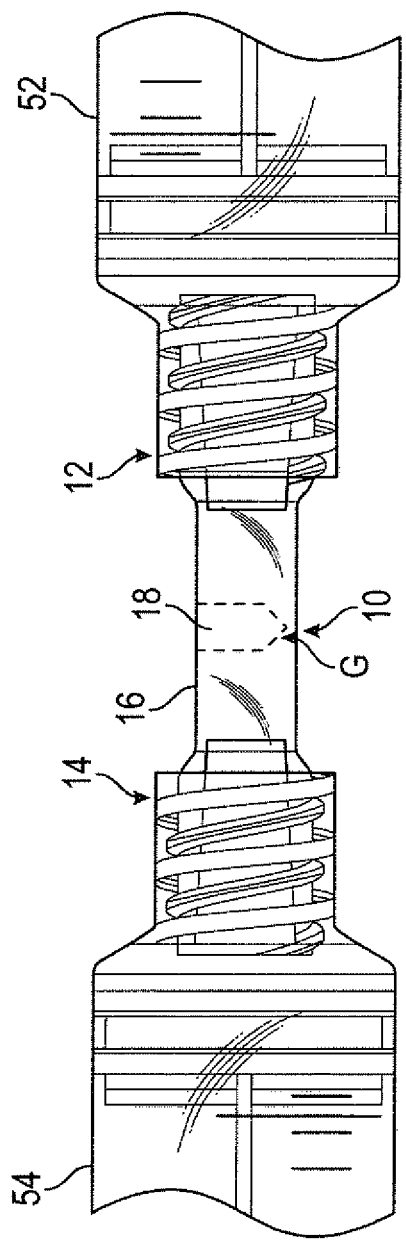
FIG. 5 is side elevation view of an embodiment of the present invention attached to a plurality of structures, each with a luer fitting.
Figure 6:
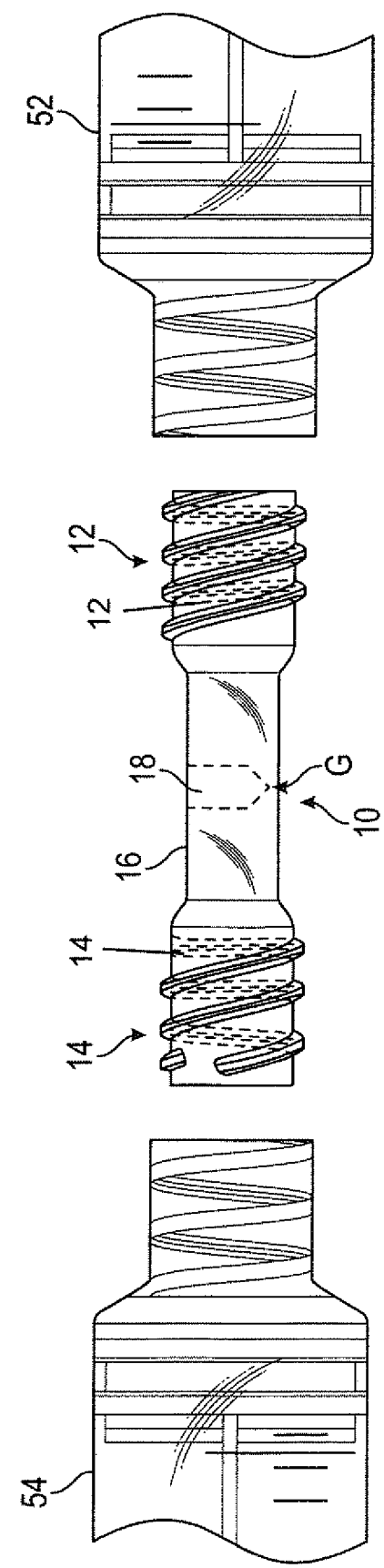
FIG. 6 is a side elevation view of an embodiment of the present invention spaced apart from a plurality of structures, each with a luer fitting.

Often, a structure has a liter fitting comprising an inner hollow core, within which is the liquid flow path, extends and protrudes from an outer hollow sleeve, with the inner core forming a tip, such as the luer fittings 52 and 54 shown in FIGS. 4 and 5, with the inner wall of the sleeve having positioned thereon a plurality of threads. Such a structure, often referred to as a threaded luer lock tip, threaded Luer tip, or simply luer tip (such structure hereinafter "luer tip structure"), is attachable to a morselizer end section 12/14 comprising a luer fitting having a plurality of threads formed on the outer wall of such end section 12/14 (male luer fitting), with such end section 12/14 threadedly attached to the luer tip structure 52/54, wherein the plurality of threads of male luer fitting of end section 12/14 are complementarily mateable to the plurality of threads on the inner wall of the sleeve of the luer tip structure luer fitting 52/54, with the end section 12/14 of morselizer 1 (i) accommodating therein the core of the luer tip structure luer fitting 52/54 and (ii) accommodated within the sleeve of the luer tip structure luer fitting 52/54.

In another embodiment of the invention, a morselizer end section 12/14 comprising a luer fitting having a plurality of threads formed on the inner wall of such end section 12/14 is attachable to a structure 52/54 with a luer tip fitting 52/54, with frictional forces between morselizer 1 and the structure 52/54 maintaining the end section 12/14—structure 52/54 attachment.

With reference to FIGS. 1-9, positioned in center section 16 is one or more blades 18, preferably one blade 18. With reference to FIG. 1, each of the one or more blades 18 is a planar structure defined by posterior and anterior ends and at least two side ends wherein at least two ends, preferably the two side ends, comprise cutting ends, such blade 18 comprising (i) a first end 182 proximal first end section 12 and preferably comprising a cutting end, (ii) a posterior end 186 secured to morselizer 10 at center section 16, (iii) a second end 184 proximal second end section 14 and preferably comprising a cutting end, and (iv) an anterior end 185 positioned in the hollow interior of morselizer 10 at center section 16, preferably comprising a cutting end, more preferably ending at a point. Such one or more blades 18 extends transversally from the blade posterior end 186 at a center section inner wall first position across the inner diameter of center section 16 to the blade anterior end 185 to a position short of a center section inner wall second position opposite the center section inner wall first position, leaving a gap G between the blade anterior end 185 and the center section inner wall second position.

In a preferred embodiment, posterior blade end 186 is secured to morselizer 10 inner wall at center section 16 by a glass-to-metal seal. More preferably, posterior blade end 186 extends through morselizer 10 inner wall with a glass-to-metal seal formed in the glass matrix between the inner and outer walls of morselizer 10 at center section 16. Additionally and preferably, the one or more blades 18 are axially positioned toward the axial midpoint of morselizer 10 at center section 16, preferably with at least one of the one or more blades 18 axially positioned at the axial midpoint of morselizer 10 at the center section 16 axial midpoint.

Each of the one or more blades 18 positioned in center section 16 comprises any blade type known in the art. Preferably, at least one of the one or more blades 18 comprises a scalpel blade, more preferably, a double-sided scalpel blade 18 with first end 182 proximal first end section 12 and second end 184 proximal second end section 14 wherein first cutting 182 and second cutting edge 184 each extend transversally across center section 16 and taper toward each other forming anterior end 185 and ending at a blade point proximal the inner diameter of center section 16.

The morselizer allows for atraumatic resizing of material through axial liquid transfer through the axial liquid pathway of the morselizer by (I) attaching a first structure with a Luer fitting containing material in a liquid solution to the morselizer by attaching the first structure luer fitting to the morselizer luer fitting at the first end section of the morselizer and attaching a second structure with a luer fitting to the morselizer luer fitting at the second end of the morselizer; and (II) transferring material in the liquid solution from the first structure to the morselizer through the first structure-morselizer luer fitting attachment, thence through the morselizer center section where material is resized by the one or more blades positioned in the morselizer center section and through the second end section of the morselizer to the second structure through the second structure-morselizer luer fitting attachment; and, as needed or desired the user depending on the given size of the diameter and the desired size of the diameter, (III) successively transferring material in the liquid solution from the second structure through the morselizer to the first structure and thence back to the second structure through the morselizer as discussed above at (II). The desired size of the atraumatically resized material is determined in large part by the size of the gap G separating the one or more blades 18 and the center section 16 inner wall, with the average diameter of the desired material approximating the size of the gap G.

Although the description above contains much specificity, such description specificity should not be construed as limiting the scope of the embodiments of the invention but as merely providing illustrations of some of the presently-preferred embodiments. Thus, the scope of the invention should be determined by the appended claims and their legal equivalents, rather than by the examples given.

I claim:

1. A morselizer comprising:

a. a hollow cylindrical structure with an inner wall and an outer wall and comprising a first end section, a second end section, and a center section extending axially between the first end section and the second end section providing an axial liquid pathway therein;

b. wherein each end section comprises an axially and radially hollow luer fitting that is attachable to a structure with a complementarily sized luer fitting;

c. wherein the first end section comprises a threaded female-male luer fitting with a plurality of threads formed on the first end section inner wall and the first end section outer wall;

d. wherein the second end section comprises a threaded female-male luer fitting with a plurality of threads formed on the second end section inner wall and the second end section outer wall; and e. one blade extending transversally across the inner diameter of the center section wherein (i) the blade is comprised of a plurality of ends, including a posterior end secured with a glass-to-metal seal between the inner wall of the center section and the outer wall of the center section at a midpoint of the center section and an anterior end extending straight down from the posterior end, a gap positioned between the anterior end and the inner wall of the center section, the gap equal in size to a desired diameter of material to flow through the morselizer, and (ii) a pair of cutting edges, wherein a first cutting edge is proximal the first end section and a second cutting edge is proximal the second end section, the first cutting edge and the second cutting edge each extend transversally across the center section and taper inward forming the anterior end.

2. A morselizer as claimed in claim 1, wherein the second end section comprises a threaded collared luer fitting comprising a collar comprised of a cylindrical structure with an inner wall and an outer wall, said collar attached to and overlaying the second end section outer wall, wherein the collar has a plurality of threads formed on the collar inner wall and is freely rotatable and partially axially displaceable from the second end section outer wall and attachable to a complementarily sized threaded luer fitting on a structure forming a rotating collar luer lock attachment between the morselizer second end section and the structure luer fitting.

3. A morselizer as claimed in claim 1, wherein the second end section comprises a luer fitting selected from the group consisting of (i) an unthreaded luer fitting attachable to a complementarily sized unthreaded luer fitting on a structure forming a luer slip attachment between the morselizer end section and the structure luer fitting, or (ii) a male-female luer fitting with a plurality of threads formed on the end section inner wall and a plurality of threads formed on the end section outer wall.

4. A morselizer as claimed in claim 1, wherein the center section has a diameter in a range of 2 to 5 mm.

5. A morselizer as claimed in claim 1, wherein the center section has a diameter in a range of 3 to 4 mm.

* * * * *